(12) United States Patent
Liu et al.

(10) Patent No.: US 11,617,557 B2
(45) Date of Patent: Apr. 4, 2023

(54) FAST 3D RADIOGRAPHY USING MULTIPLE PULSED X-RAY SOURCES IN MOTION WITH C-ARM

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AIX Scan, Inc., Sunnyvale, CA (US)

( * ) Notice: Subject to any disclaimer, the term of this patent is extended or adjusted under 35 U.S.C. 154(b) by 81 days.

(21) Appl. No.: 17/497,231

(22) Filed: Oct. 8, 2021

(65) Prior Publication Data
US 2022/0313187 A1    Oct. 6, 2022

Related U.S. Application Data

(60) Provisional application No. 63/226,508, filed on Jul. 28, 2021, provisional application No. 63/225,194, (Continued)

(51) Int. Cl.
*A61B 6/00* (2006.01)
*A61B 6/02* (2006.01)
(Continued)

(52) U.S. Cl.
CPC .............. *A61B 6/541* (2013.01); *A61B 6/025* (2013.01); *A61B 6/032* (2013.01); *A61B 6/035* (2013.01); *A61B 6/0407* (2013.01); *A61B 6/06* (2013.01); *A61B 6/08* (2013.01); *A61B 6/405* (2013.01); *A61B 6/4007* (2013.01); *A61B 6/4014* (2013.01); *A61B 6/4021* (2013.01);
(Continued)

(58) Field of Classification Search
CPC ........ A61B 6/4007; A61B 6/032; A61B 6/025
See application file for complete search history.

(56) References Cited

U.S. PATENT DOCUMENTS

| 2009/0080598 A1* | 3/2009 | Tashman | A61B 5/1038 |
| | | | 378/11 |
| 2010/0172561 A1* | 7/2010 | Ota | G01N 23/046 |
| | | | 378/19 |

(Continued)

*Primary Examiner* — Dani Fox
(74) *Attorney, Agent, or Firm* — Patent PC; Bao Tran

(57) ABSTRACT

A C-Arm X-ray imaging system using multiple pulsed X-ray sources in motion to perform efficient and ultrafast 3D radiography is presented. X-ray sources mounted on a structure in motion to form an array. X-ray sources move simultaneously relative to an object on a pre-defined arc track at a constant speed as a group. Each individual source can also move rapidly around its static position in a small distance. When a source has a speed that is equal to group speed but with opposite moving direction, the source at one C-arm end and X-ray flat panel detector at other C-arm end are activated through an external exposure control unit so that source stay momentarily standstill. The C-arm provides 3D X-ray scan imaging over a wide sweep angle and in different position by rotation. The X-ray image can be analyzed by an artificial intelligence module for real-time diagnosis.

20 Claims, 4 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.

| | | |
|---|---|---|
| *G06T 17/00* | (2006.01) | |
| *G01N 23/044* | (2018.01) | |
| *A61B 6/03* | (2006.01) | |
| *A61B 6/06* | (2006.01) | |
| *G01N 23/083* | (2018.01) | |
| *G01N 23/18* | (2018.01) | |
| *G06T 7/00* | (2017.01) | |
| *G06T 11/00* | (2006.01) | |
| *A61B 6/04* | (2006.01) | |
| *G06T 7/11* | (2017.01) | |
| *G16H 10/60* | (2018.01) | |
| *G16H 30/20* | (2018.01) | |
| *G16H 50/20* | (2018.01) | |
| *G06V 10/25* | (2022.01) | |
| *G06V 10/62* | (2022.01) | |
| *A61B 6/08* | (2006.01) | |

(52) U.S. Cl.
CPC .......... *A61B 6/4208* (2013.01); *A61B 6/4283* (2013.01); *A61B 6/4405* (2013.01); *A61B 6/4441* (2013.01); *A61B 6/4452* (2013.01); *A61B 6/4476* (2013.01); *A61B 6/4482* (2013.01); *A61B 6/467* (2013.01); *A61B 6/482* (2013.01); *A61B 6/54* (2013.01); *A61B 6/542* (2013.01); *A61B 6/56* (2013.01); *A61B 6/583* (2013.01); *G01N 23/044* (2018.02); *G01N 23/083* (2013.01); *G01N 23/18* (2013.01); *G06T 7/0012* (2013.01); *G06T 7/0016* (2013.01); *G06T 7/11* (2017.01); *G06T 11/003* (2013.01); *G06T 11/006* (2013.01); *G06T 17/00* (2013.01); *G06V 10/25* (2022.01); *G06V 10/62* (2022.01); *G16H 10/60* (2018.01); *G16H 30/20* (2018.01); *G16H 50/20* (2018.01); *A61B 6/4275* (2013.01); *A61B 6/502* (2013.01); *G01N 2223/401* (2013.01); *G06T 2200/24* (2013.01); *G06T 2207/10076* (2013.01); *G06T 2207/10081* (2013.01); *G06T 2207/20081* (2013.01); *G06T 2207/20084* (2013.01); *G06T 2207/30064* (2013.01); *G06T 2207/30096* (2013.01); *G06T 2207/30168* (2013.01); *G06T 2210/41* (2013.01); *G06V 2201/032* (2022.01)

(56) References Cited

U.S. PATENT DOCUMENTS

2012/0076260 A1* 3/2012 Kitagawa ............... G16H 30/40
  382/128
2020/0345318 A1* 11/2020 Turner ................... A61B 6/587

\* cited by examiner

FAST 3D RADIOGRAPHY USING MULTIPLE PULSED X-RAY SOURCES IN MOTION WITH C-ARM

The present invention claims priority to Provisional Application Ser. Nos. 63/182,426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

This patent specification is in the field of C-arm X-ray imaging systems and methods, and is particularly applicable to using pulsed X-ray source and large field, X-ray digital flat panel detectors.

BACKGROUND

C-shaped arm (C-arm) X-ray imaging systems are currently used in medical, NDT, and even security applications to create primarily two-dimensional x-ray projection images. Like other cone-beam X-ray imaging devices, conventional C-arm X-ray imaging systems are usually equipped with one X-ray source, one X-ray flat panel detector, and a movable stage. Firstly, a C-arm X-ray imaging system includes an x-ray source mounted to one end of a C-arm, and an X-ray detector mounted to an opposite end of the C-arm. The X-ray detector includes a detector mount and a movable stage to move within the detector mount. Secondly, an X-ray detector for an imaging system includes a detector mount capable of being coupled with a C-arm. The X-ray detector also has a movable stage coupled to the detector mount that is operable to translate along with the detector mount. Thirdly, a method of imaging employs a C-arm X-ray imaging system. The method includes positioning a movable stage of an X-ray detector at a first position, performing a first partial circular scan to acquire the first set of projection data, repositioning the movable stage of the X-ray detector to a second position offset from the first position, and performing a second partial circular scan to acquire a second set of projection data. C-arms have radiographic capabilities, though used primarily for fluoroscopic intraoperative imaging during surgical, orthopedic, and emergency care procedures. Fluoroscopy is a type of medical imaging that shows a continuous X-ray image on a monitor, much like an X-ray movie.

However, there is a major disadvantage of the existing conventional C-arm X-ray imaging system. The continuous conventional C-arm X-ray images are 2D images, not 3D images. In order to obtain a better view of organs, blood vessels, tissues, and bones, sometimes C-arm has to be repositioned. In addition, C-arm size is usually large and heavy. Put into position to take images would need some time. If C-arm is used for 3D CT, the object or patient has to be standstill during the entire X-ray image acquisition.

Current invention suggests a much faster, lower-cost C-arm 3D X-ray imaging system by using multiple pulsed X-ray sources in motion. It can do tomosynthesis at a much faster speed. X-ray imaging can also be taken using artificial intelligence.

SUMMARY

In a first aspect, a C-arm X-ray system to provide fast 3D radiography using multiple pulsed X-ray sources in motion with a primary motor stage moving freely on an arc rail with a predetermined shape; a primary motor that engages with said primary motor stage and controls a speed of the primary motor stage; a plurality of secondary motor stages coupled to said primary motor stage and move along a direction of the arc rail; a plurality of secondary motors, each engaging a secondary motor stage and controlling a speed of secondary motor stage; a plurality of X-ray sources each moved by a secondary motor stage; a supporting frame structure that provides housing for the primary motor stage and secondary motor stages; and a flat panel detector to receive X-ray imaging data.

In a second aspect, a method of C-arm fast 3D radiography using multiple pulsed X-ray sources in motion includes positioning a primary motor stage and one or more secondary motor stages to a predetermined initial location; sweeping the primary motor stage at a predetermined constant speed by said primary motor; oscillating each of the secondary motor stages by a corresponding secondary motor with a predetermined sequence; electrically activating an X-ray source and a flat panel detector when a secondary motor stage moves in an opposite direction to that of the primary motor stage and at a selected speed of the primary motor stage; and acquiring image data from the X-ray source with a flat panel.

In another aspect, a C-arm X-ray imaging system using multiple pulsed X-ray sources in motion to perform ultrafast, highly efficient 3D radiography is presented. In the system, multiple pulsed X-ray sources are mounted on a structure in motion to form an array of the source. The multiple X-ray sources move simultaneously around an object on a pre-defined track at a constant speed of a group. Each individual X-ray source can also move rapidly around its static position of a small distance. When an individual X-ray source has a speed that equals to group speed but an opposite moving direction, the individual X-ray source is triggered through an external exposure control unit. This arrangement allows the X-ray source to stay relatively standstill during the X-ray pulse trigger exposure duration. Multiple X-ray sources result in a much-reduced source travel distance for individual X-ray sources. X-ray receptor is an X-ray flat panel detector. 3D radiography image projection data can be acquired with an overall much wider sweep in a much shorter time, and image analysis can also be done in real-time while the scan goes.

In another aspect, a C-arm X-ray imaging system using multiple pulsed X-ray sources in motion to perform highly efficient and ultrafast 3D radiography includes multiple pulsed X-ray sources mounted on a structure in motion to form an array of sources. The multiple X-ray sources move simultaneously relative to an object on a predefined arc track at a constant speed as a group. Each individual X-ray source can also move rapidly around its static position at a small distance. When an individual X-ray source has a speed equal to group speed, but with opposite moving direction, the individual X-ray source and X-ray detector are activated through an external exposure control unit.

Advantages of the instant method and system may include one or more of the following. The arrangement allows the X-ray source to stay relatively standstill during the X-ray source activation and X-ray detector exposure. X-ray receptor is an X-ray flat panel detector. Multiple X-ray source in motion operation results in a much-reduced source travel distance for individual X-ray sources. 3D radiography image data can be acquired with an overall wider sweep angle in a much shorter time, and image analysis can also be done in real-time while the scan goes. In implementations, the X-ray can also be randomly activated from one of any sources in the array using a random-firing scheme. Results of each and accumulated analysis determine the next X-ray source and exposure condition. 3D X-ray radiography images with C-arm are reconstructed based on each image with an angled geometry of the X-ray exposure source. Much broader applications include 3D mammography or tomosynthesis, chest 3D radiography for COVID or fast 3D NDT, fast 3D X-ray security inspection.

BRIEF DESCRIPTION

DETAILED DESCRIPTION

In the following paragraphs, the present invention will be described in detail by way of example with reference to the attached drawings. Throughout this description, the preferred embodiment and examples shown should be considered exemplars rather than limitations on the present invention. As used herein, the "present invention" refers to any one of the embodiments of the invention described herein and any equivalents. Furthermore, reference to various feature(s) of the "present invention" throughout this document does not mean that all claimed embodiments or methods must include the referenced feature(s).

Figure 1:
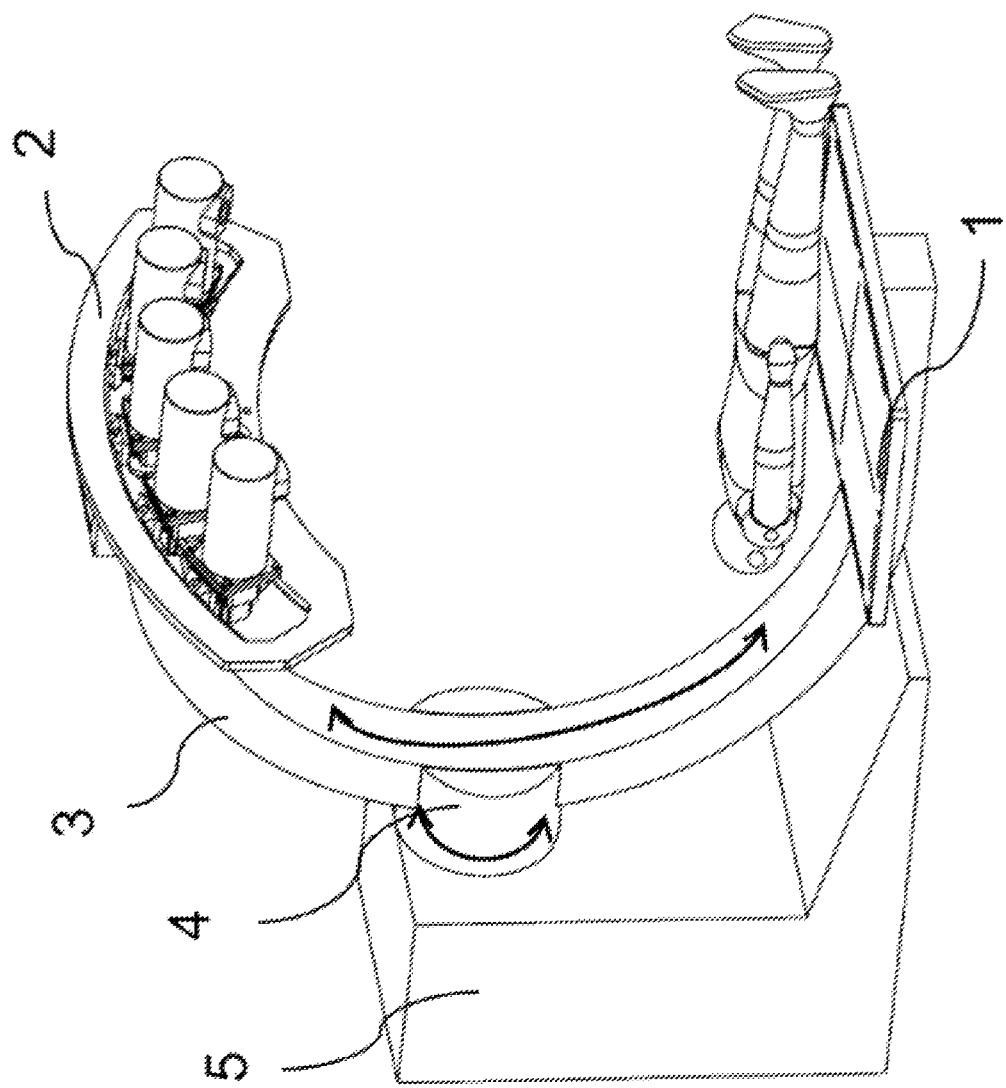
FIG. 1 illustrates an exemplary C-arm X-ray imaging system using multiple pulsed X-ray sources in motion.

A novel ultrafast 3D C-arm digital imaging system with multi pulsed X-ray sources is shown in FIG. 1. It comprises a primary motor 6 engaged with a primary motor stage 7, multiple X-ray sources 10, and an X-ray flat panel detector 1. All motors, all motor stages, and X-ray sources are mounted in a supporting multi pulsed source frame structure 2. Frame structure 2 is mounted at one end of C-arm 3, while an X-ray detector 1 is mounted at the other end of C-arm 3. The C-arm 3 has its own C-arm rotation motor 4 and C-arm support 5. More degree of freedom can be added by adding more motion controls. For example, supporting multi pulsed source frame structure 2 itself can rotate if another motor is added at C-arm 3 etc.

An object to be imaged is usually put on a movable stage. Each secondary motor 8 is engaged to a secondary motion stage 9. All secondary motion stages 8 are mounted on a primary motion stage 7. Every X-ray source 10 is mounted on a secondary motor stage 9. Every motor is controlled by programmable motion control hardware and can move the motor stage back and forth at a predetermined speed. The secondary motor stages 9 are positioned in such a way that spacing to adjacent stages is equal. As a result, all X-ray sources 5 move together with the primary motor stage 7, but each individual X-ray source 10 can also move individually with the secondary motor stage 9. The X-ray flat panel detector 1 can also be mounted on an additional linear stage. The X-ray flat panel detector 1 can move back and forth, based on the location of X-ray sources 10 in order to have a broader coverage of images.

The X-ray flat panel detector 1 is used to provide an X-ray image of an object in motion for 3D radiography using multiple pulsed X-ray sources in motion with a primary motor stage 7 moving freely on an arc rail with a predetermined shape. A primary motor 6 that engages with said primary motor stage 7 and controls the speed of the primary motor stage 7. A plurality of secondary motor stages 9 coupled to said primary motor stage 7 moves along the arc rail direction. A plurality of secondary motors 8 each engaging a secondary motor stage 9 and controlling the speed of the secondary motor stage 9. A plurality of X-ray sources 10 is mounted on a structure in motion to form an array of the source. A frame structure 2 provides support housing for the primary motor 6, primary motor stage 7, secondary motor 8, secondary motor stages 9.

Multi pulsed source frame structure 2 provides support for the X-ray system that includes the primary motor stage 7, secondary motor stages 9, and the multiple X-ray sources 10. It is assembled from a combination of laser-cut frames sheet metal and high strength linear ball bearings to provide precise rotation positioning and smooth moving at a constant speed for the X-ray system. With the ability to be broken down into parts to facilitate shipping and installation, the mainframe is mounted on an off-the-shelf articulated robotic platform that can be used to move the entire system. A supporting frame structure 2 provides housing for the primary motor stage 8 and secondary motor stages 9 and includes a bottom section for primary motor stage 8, a top section for secondary motor stages 9, and an inter frame coupling mechanism between the bottom section and the top section.

The frame structure 2 at C-arm 3 includes an arc rail that provides linear movement along a line. The rail is moved by a motor along the length of the arc rail. In this aspect, C-arm X-ray system provides fast 3D radiography using multiple pulsed X-ray sources in motion with a primary motor stage 7 moving freely on an arc rail with a predetermined shape. The primary motor 6 engages with said primary motor stage 7 and controls a speed of the primary motor stage 6, while a plurality of secondary motor stages 9 coupled to said primary motor stage 7 moves the assembly along a direction of the arc rail. As to the plurality of secondary motors 8, each engages a secondary motor stage 9 and controls speed of the secondary motor stage 9.

C-arm rotation motor 4 rotates the C-arm assembly about an object under inspection. X-ray source 10 or array of X-ray sources 10 moves relative to the C-arm at a predetermined speed forming an array of sources in motion. A single pulsed X-ray source can be activated from any source in the array or even from all sources simultaneously. Each X-ray pulse results in corresponding projection data by selecting the first and last position in time for the scan data and stitching many individual image slices with a computer program.

C-arm support 5 is designed to allow various motor stages to move freely on an arc rail along the predetermined track and have an angular shape. A primary motor 6 drives the primary motor stage 7 through gears. The primary motor stage 7 provides a pivot for a secondary motor stage to oscillate back and forth at the selected oscillation frequency. Each secondary motor stage has a secondary motor mounted on it and electrically connected to an external exposure control unit. Each of the secondary motor stages 9 moves with its corresponding secondary motor 8 to provide fast movement in the sweep direction forward or backward at a selected speed controlled by the corresponding secondary motor excerpt from the claims. C-arm X-ray system using multiple pulsed X-ray sources in motion to perform ultrafast high-efficient 3D radiography comprising multiple pulsed X-ray sources are mounted on a structure in motion to form an array of sources.

In sum, the system includes a plurality of X-ray sources 10 moved by a secondary motor stage 9, a supporting frame structure 2 that provides housing for the primary motor 6, primary motor stage 7 and secondary motor 8 and secondary motor stages 9. This system has many advantages. First, the configuration has less stress on moving parts such as a gear or pinion. Second, the direction of the movement is easy to change as long as there is a different path between the same points. This enables X-ray imaging to form complex geometries without much effort in the overall configuration. Third, the array can be very wide, and yet individual sources stay relatively stationary during operation.

Figure 2:
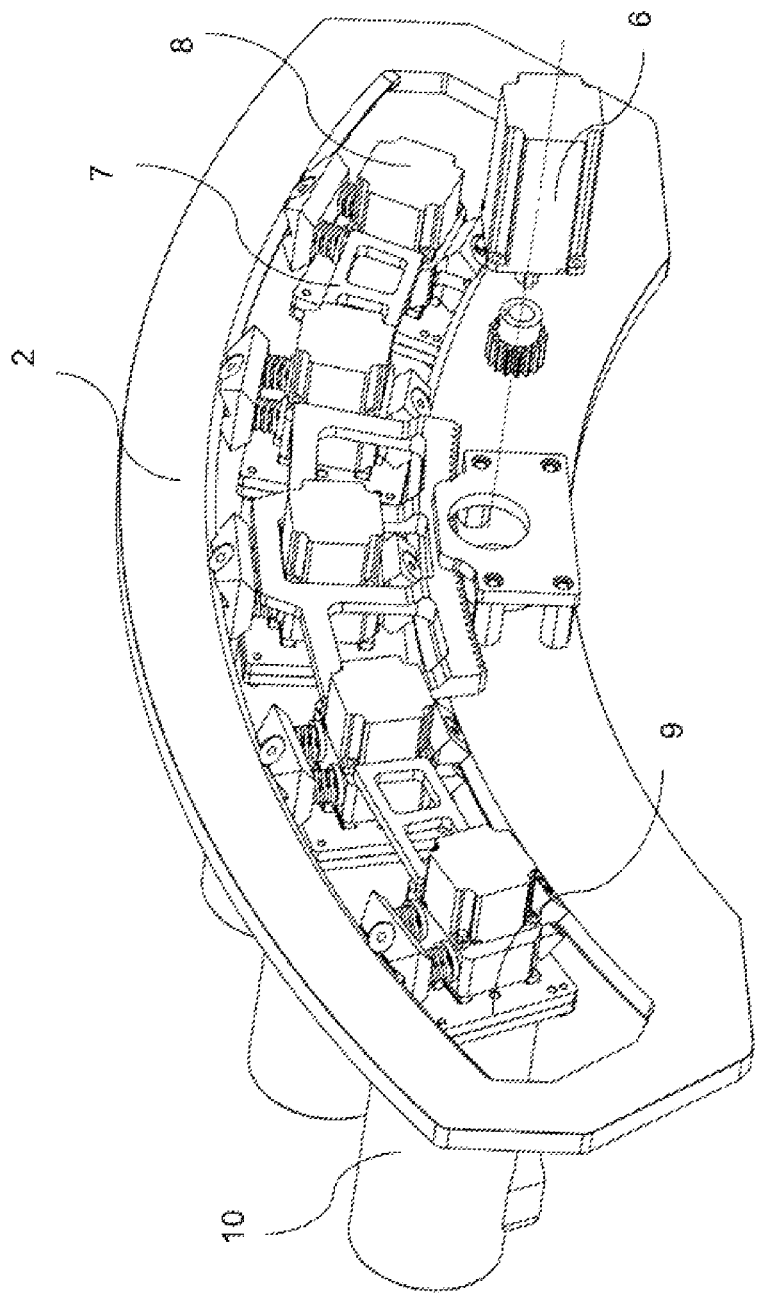
FIG. 2 illustrates exemplary placement of X-ray sources with motion control.

FIG. 2 illustrates an exemplary placement of X-ray sources 10 with motion control. In this exemplary embodiment, secondary motors 8 are interconnected as an assembly of rigid body structure that serves as a primary motor stage 7 because it has rolling wheels at the edges. Primary motor 6 engages primary motor stage 7 by gears. Primary motor 6 can move primary motor stage 7 along the rigid rail at a predetermined constant speed. Because all secondary motion stages 9 are mounted one structure, they can also move along the rigid rail at a predetermined constant speed. Secondary motor 8 are equally spaced to their neighbor secondary motors 8. Each secondary motor stage 9 can move back-and-forth by a secondary motor 8. An X-ray source 10 is mounted on a secondary motor stage 9. The motion of each X-ray source 10 on a secondary motor stage 9 has four sessions of motion: acceleration, constant speed, deceleration, and move back to the initial position. At any moment, only one X-ray source 10 can be on a constant speed that moves opposite direction to primary motor stage 7. The momentary constant speed of a secondary motor stage 9 is programmed to be equal to the constant motion speed of the primary motor stage 7.

Primary motor 6 is engaged with a primary motor stage 7. The primary motor stage 7 moves freely on an arc rail with a predetermined shape, for example, a circular shape. The primary motor 6 of the C-arm X-ray system moves along the arc rail with a predetermined speed. The primary motor stage 7 is configured to support secondary motor stages 9. Each of the secondary motor stages 9 has one X-ray source 10 mounted. Multiple secondary motor stages 9 allow high-efficient and ultrafast 3D radiography imaging to be performed.

Primary motor stage 7 moves freely on an arc rail by a primary motor 6. It has multiple X-ray sources 10 in a predetermined position. The primary motor stage 7 is set to a first initial location. Multiple secondary motor stages 9 are coupled to the primary motor stage 7 and moved simultaneously with the primary motor stage 7 in the direction of the arc rail.

Secondary motor stage 9 is driven by a secondary motor 8 with a rotational motion or linear motion. The secondary motor stage 9 is located at the top of the X-ray sources 10 such as an X-ray tube and thus may move above. All X-ray sources 10 travel linearly along the arc rail in a constant speed. A pulse train generator may activate each X-ray source 10 individually or simultaneously during a burst exposure time.

Secondary motor stage 9 can change its angular velocity to about a maximum value determined by the gearing ratio. The motor is typically operated with its maximum angular velocity, as a result travel distance of X-ray source 10 can be significantly reduced. Multiple X-ray sources 10 on multiple motor stages make up an array that operates together when the primary motor stage 7 rotates along arc rail with a constant speed. The group of X-ray sources 10 follows with a same angular velocity and direction of motion. When one of the secondary motor stages 9 moves in the opposite direction to that of the primary motor stage 7 and with a selected speed of the primary motor stage the X-ray source 10 coupled to the secondary motor stage 9 is activated through a control unit. 3D radiography images are acquired using an X-ray flat panel detector 1 while the X-ray sources follow a moving track around the object under examination.

X-ray source 10 is mounted on a support structure in motion and located adjacent to an object under examination. Multiple X-ray sources 10 can be arranged on the support structure and move simultaneously around the object. As one example, each individual X-ray source 10 moves randomly at a small distance within a range from a static position when it has a speed that equals to group speed, but with the opposite moving direction, this arrangement allows the X-ray source 10 to stay relatively standstill during the X-ray source activation and X-ray detector exposure. Multiple X-ray sources 10 result in a much-reduced source travel distance for individual X-ray sources 10. 3D radiography image data can be acquired with an overall wider sweep angle in a much shorter time, and image analysis can also be done in real-time while the scan goes.

Figure 3:
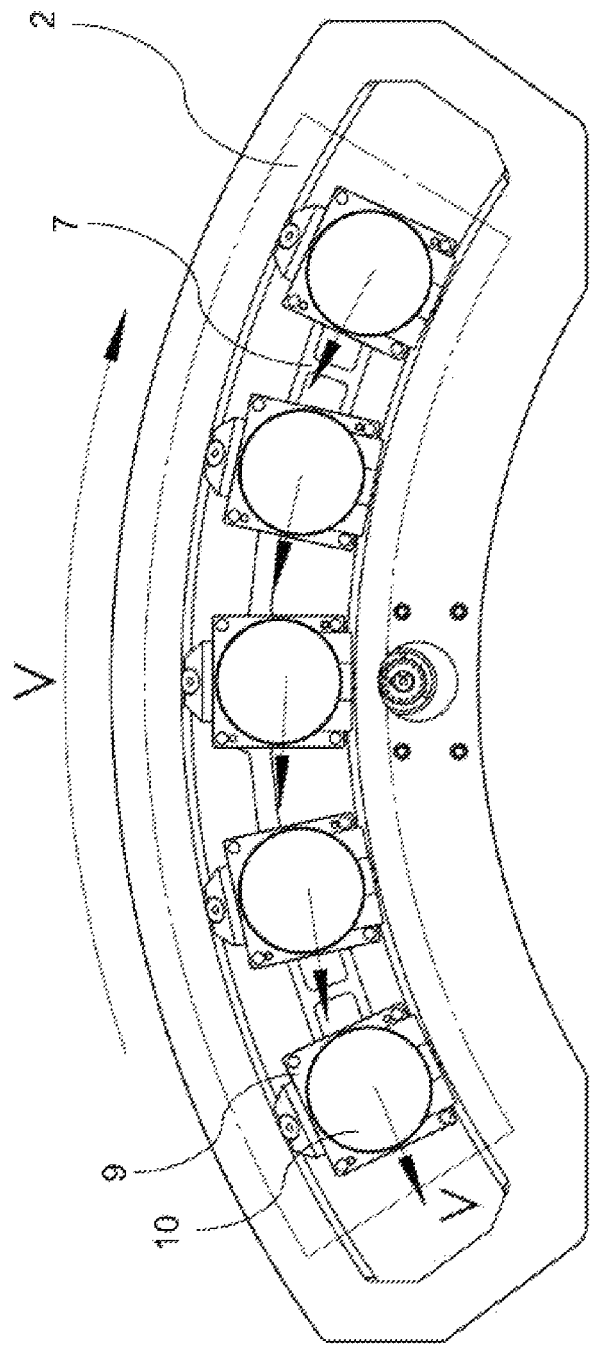
FIG. 3 illustrates an exemplary configuration where an individual X-ray source emits an X-ray beam in a momentary standstill position at the moment when the primary and secondary motor stages are moving in the opposite direction but at the same speed.

FIG. 3 illustrates an exemplary configuration where an individual X-ray source 10 emits an X-ray beam in a temporary standstill position when the primary motor stage 7 and secondary motor stages 9 are moving in the opposite direction but with the same speed. It shows how motion control operation is performed. For one data acquisition cycle, primary motor stage 7 moves in one direction at a constant speed, then go back to the initial position. While primary motor stage 7 is moving at a constant speed, secondary motor stage 9 vibrates at the predetermined speed. When secondary motor stage 9 travels in the opposite direction to the primary motion stage 7 and has the same constant speed, X-ray source 10 and X-ray flat panel detector 1 are triggered. At this moment of a trigger, an X-ray source 10 behaves like the X-ray source 10 is standstill while emitting an X-ray beam. Therefore, the dynamic arrangement of stationary state an X-ray source 10 allows an X-ray imaging system to acquire a large number of images from different spatial angle locations in a very short amount of time. Duration of constant speed motion of a secondary motor stage 9 can be programmed by software to match X-ray exposure time. When one secondary motor stage 9 is at the constant speed, the other secondary motor stage 9 could be in acceleration, deceleration, or move back to the initial position in order to get ready for their next constant speed. X-ray sources 10 can also be programmed to perform exposure on-demand based on each independent external trigger pulse in a random sequence.

Primary motor stage 7 moves freely on an arc rail of a predetermined shape, such as circular or elliptical. The primary motor stage 7 can be implemented as a linear moving stage. In one embodiment primary motor drives the primary motor stage 7 and controls a speed of the primary motor stage 7. Secondary motor stages 9 and are coupled to the primary motor stage 7 and move along a direction of the arc rail at a constant speed with respect to the primary motor stage 7. The secondary motor stages 9 and are mechanically coupled to the primary motor stage 7 through gears, belts or chains.

Secondary motor stage 9 can move in any direction and rotate around the pivot point on the track. Secondary motor stage 9 is engaged to a secondary motor 8. The motor is controlled by control unit for example an electrical current from power supply flows into primary winding of motor through contact and then exits from primary winding through contact to form a magnetic field in the windings of motor. This arrangement allows motor to operate to generate torque and drive the secondary motor stage 9 to move along the arc rail in either direction.

Figure 4:
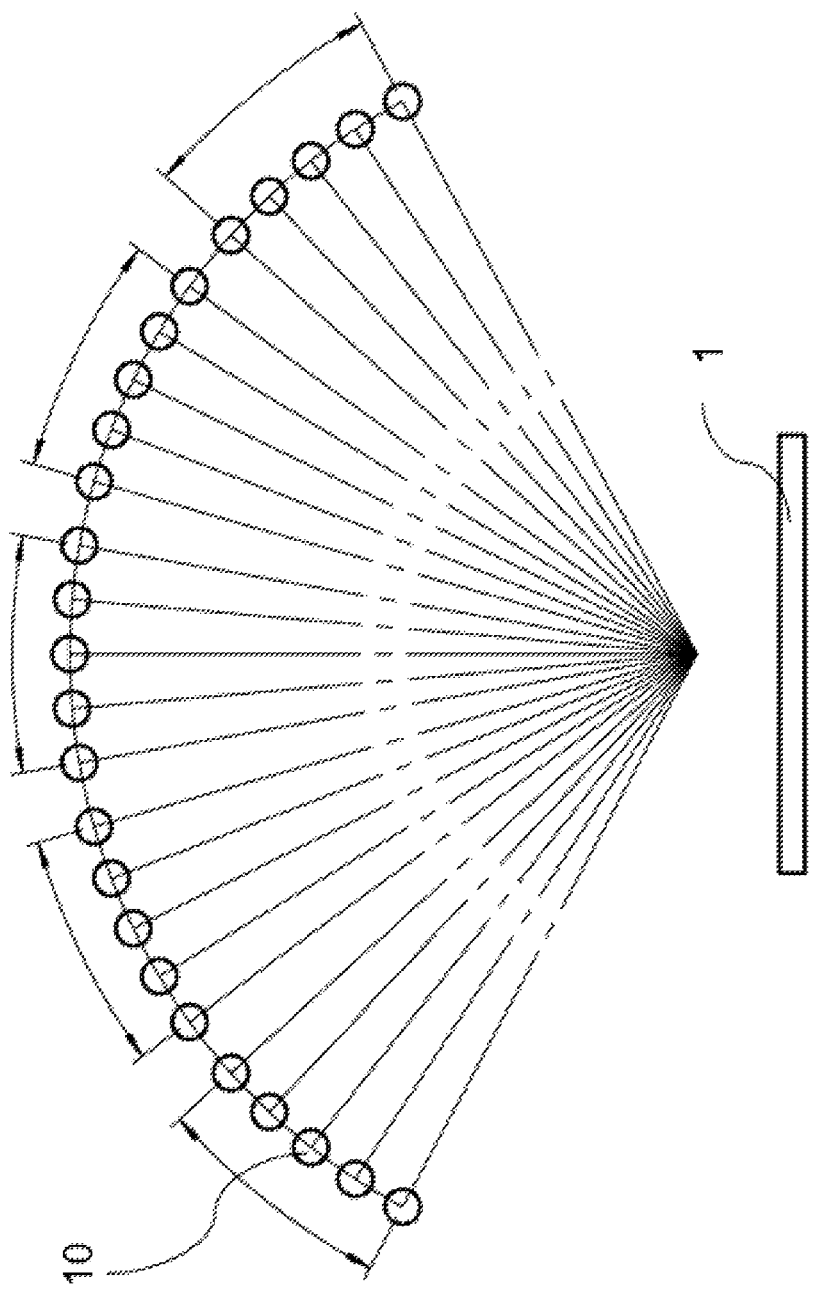
FIG. 4 illustrates an exemplary five-X-ray-source system taking 25 sets of projection data, each traveling only one-fifth of the total distance.

FIG. 4 illustrates how a five X-ray source system can take 25 sets of projection data by each traveling only one-fifth of the total distance. In this example, the five X-ray sources 10 perform total 25 X-ray exposures at different angle positions. Due to the placement of the five sources, each secondary motor stage 9 only needs to travel one-fifth of the total covered angle. Therefore, with multiple X-ray sources 10 working in parallel, a large amount of projection data can be acquired at a fraction of the amount of time. X-ray flat panel detector 1 serves as an X-ray receiver. Electronic signals always go faster than of mechanical motion, bottleneck of the limiting factor is always motor stage motion itself. The next bottleneck is detector readout limitation. Because detector also needs some time to read out many Megapixel data and then transfer to a computer. With a high-speed processor and GPU, image analysis can be done in real-time with the image acquisition. Judgment on the images taken will have an impact on the X-ray source 10 positions for the next shot. There is no need to wait until finish of the whole image acquisition to do image reconstruction.

In another embodiment, the system uses multiple pulsed X-ray sources in motion to perform ultrafast, high-efficient 3D radiography. Radiographic images of a patient are captured in real-time. The system includes a source driver that supplies voltage and triggers pulses to X-ray sources. A primary motor stage is coupled to the source driver to move the source. A supporting frame structure that provides housing for the primary motor stage and secondary motor stages and a flat panel detector. The primary motor stage includes a primary motor, a gear mechanism, and a linear guide rail. The secondary motor stages each include a secondary motor, a ball screw drive, around rail a timing belt. X-ray flat panel detector 1 provides X-ray detector image data for a C-arm X-ray system.

X-ray sources 10 are mounted on a structure in motion to form an array of sources. X-ray sources move simultaneously relative to an object on a predefined arc track at a constant speed as a group. Each individual X-ray source can also move rapidly around its static position at a small distance. When an individual X-ray source has a speed that is equal to group speed but with opposite moving direction, the X-ray source 10 at one C-arm end and X-ray flat panel detector 1 at other C-arm end are activated through an external exposure control unit so that source stay momentarily standstill. The primary motor stage moves freely on an arc rail. A plurality of secondary motor stages is coupled to the primary motor stage and moves along the arc rail direction. The primary motor stage is mounted on an arc rail having a predetermined shape and includes a motor unit, a base supporting the motor unit, and a connecting rod coupled to the base and the motor unit. The secondary motor stages are arranged in parallel and mounted on the connecting rod to be movable along the arc rail.

The individual X-ray source and X-ray detector can be activated through an external exposure control unit. This arrangement allows the X-ray source to stay relatively standstill during the X-ray source activation and X-ray detector exposure. Multiple X-ray sources result in a much-reduced source travel distance for individual X-ray sources. X-ray receptor is an X-ray flat panel detector. 3D radiography image data can be acquired with an overall wider sweep angle in a much shorter time, and image analysis can also be done in real-time. While the scan goes, multiple pulsed X-ray sources can result in 3D tomosynthesis imaging.

In yet another implementation, the C-arm X-ray system with multiple pulsed X-ray sources in motion is detailed. The system includes a primary motor stage that can move freely on an arc rail with a predetermined shape. A primary motor that engages with the primary motor stage and controls a speed of the primary motor stage. A plurality of secondary motor stages coupled to the primary motor stage and move along a direction of the arc rail. A plurality of secondary motors each engages a secondary motor stage and controls the secondary motor stage's speed. A plurality of X-ray sources, each moved by a secondary motor stage, a supporting frame structure providing housing for the primary motor and secondary motor stages, and a flat panel detector to receive X-ray imaging data. A computer-readable storage medium has instructions for executing a C-arm fast 3D radiography using multiple pulsed X-ray sources in motion, including positioning. A primary motor stage and one or more secondary motor stages to a predetermined initial location sweeping the primary motor stage at a predetermined constant speed by said primary motor oscillating. Each of the secondary motor stages by a corresponding secondary motor with a predetermined sequence electrically activating an X-ray source and a flat panel detector when a secondary motor stage moves in an opposite direction to that of the primary motor stage and at a selected speed of the primary motor stage and acquiring image data using the X-ray source with a flat panel.

Next is a discussion of an exemplary mechanical C-arm for 3D radiography in accordance with an aspect of the present invention. There are three levels of motorized X-ray sources primary motor stage moves on an arc rail. Secondary motor stages move with or opposite the primary motor stage on the arc rail, and multiple X-ray sources are mounted on each secondary motor stage. Thus, multiple X-ray sources are in motion for performing ultrafast 3D radiography with a trigger mechanism controlled by a computer control unit. The device also includes a supporting frame structure, an X-ray flat panel detector, and a fast motor stage controller. All system components are attached to the supporting frame structure for vibration-free operation. A standard C-arm imaging geometry involves the use of a swing arm. An X-ray source is located at the end of the arm, which rotates around the center axis of the human body being examined, while the detector is located on the opposite side of the rotation center axis.

In another implementation, a C-arm fast 3D radiography method uses multiple pulsed X-ray sources in motion. The method includes positioning a primary motor stage 7 and multiple secondary motor stages 9 to a predetermined initial location sweeping. The primary motor stage 7 operates at a predetermined constant speed by the primary motor 6. Each of the secondary motor stages 9 moves by a corresponding secondary motor 8 with a predetermined sequence. The method also includes electrically activating an X-ray source 10 that exposes images on an X-ray flat panel detector 1. When a secondary motor stage 9 moves in an opposite direction to that of the primary motor stage 7, the method then acquires image data using the X-ray source 10 from X-ray flat panel detector 1.

While various embodiments of the present invention have been described above, it should be understood that they have been presented by way of example only and not of limitation. The various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical, or physical partitioning and configurations may be implemented to implement the desired features of the present invention. Also, a multitude of different constituent module names other than those depicted herein may be applied to the various partitions. Additionally, with regard to flow diagrams, operational descriptions, and method claims, the order in which the steps are presented herein shall not mandate that various embodiments be implemented to perform the recited functionality in the same order unless the context dictates otherwise.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

What is claimed is:

1. A system to provide fast 3D radiography using multiple pulsed X-ray sources in motion with C-arm, comprising:
   a C-shaped arm;
   a C-shaped arm motor to make C-arm rotation;
   a C-shaped arm support;
   a primary motor stage moving freely on an arc rail with a predetermined shape;
   a primary motor that engages with said primary motor stage and controls a speed of the primary motor stage;
   a plurality of secondary motor stages coupled to said primary motor stage and move along a direction of the arc rail;
   a plurality of secondary motors, each engaging a secondary motor stage and controlling speeds of secondary motor stage;
   a plurality of X-ray sources, each moved by a secondary motor stage;
   a supporting frame structure mounted to one end of a C-arm that provides housing for said primary motor, said primary motor stage, said secondary motors, said secondary motor stages and said X-ray sources; and
   an X-ray flat panel detector mounted to an opposite end of the C-arm.

2. The system of claim 1, comprising:
   a predefined track; and
   a source array including multiple pulsed X-ray source tubes mounted on a structure in motion, wherein each of the multiple pulsed X-ray source tubes moves simultaneously around an object on the pre-defined track at a constant speed of a group, and when an individual X-ray source tube has a speed that equals to group tube speed but in an opposite moving direction, the individual X-ray source tube is triggered through an exposure control unit.

3. The system of claim 1, wherein a speed or a position of the primary motor stage or secondary motor stages is adjustable by software.

4. The system of claim 1, wherein the current and voltage of an X-ray source are adjustable by software.

5. The system of claim 1, wherein exposure time of X-ray source is adjustable by software.

6. The system of claim 1, wherein the X-ray source tube standstills relative to the X-ray flat panel detector during an X-ray pulse trigger exposure duration.

7. The system of claim 1, wherein the multiple X-ray sources have a reduced source travel distance per individual X-ray source.

8. The system of claim 1, wherein the flat panel detector acquires 3D radiography image projection data with a predetermined sweep over a predetermined time period, and wherein image analysis is performed in real-time during scanning.

9. The system of claim 1, wherein each individual X-ray source moves rapidly around a static position with a predetermined distance.

10. The system of claim 1, wherein 3D X-ray radiography images are reconstructed based on each image with an angled geometry of X-ray exposure source.

11. A method to provide fast 3D radiography using multiple pulsed X-ray sources in motion with C-shaped arm, comprising:
    mounting a supporting frame structure of multiple pulsed X-ray sources to one end of a C-shaped arm;
    positioning a primary motor stage and one or more secondary motor stages to a predetermined initial location at arc rail of supporting frame structure;
    sweeping the primary motor stage at a predetermined constant speed by the primary motor;
    oscillating each of the secondary motor stages by a corresponding secondary motor with a predetermined sequence;
    electrically activating an X-ray source and an X-ray flat panel detector when a secondary motor stage moves in an opposite direction to that of the primary motor stage; and
    acquiring image data from the X-ray flat panel detector that is mounted to an opposite end of the C-arm.

12. The method of claim 11, comprising moving a stage table.

13. The method of claim 11, wherein the multiple X-ray sources have a reduced source travel distance per individual X-ray source tube.

14. The method of claim 11, wherein the X-ray source tube standstills relative to X-ray flat panel detector during an X-ray pulse trigger exposure duration.

15. The method of claim 11, wherein the X-ray source can also be randomly activated from one of any sources in the array using a random-firing scheme.

16. The method of claim 11, wherein 3D X-ray radiography images are reconstructed based on each image with an angled geometry of X-ray source.

17. The method of claim 11, wherein the flat panel detector acquires 3D radiography image projection data with a predetermined sweep over a predetermined time, and wherein image analysis is performed in real-time during scanning.

18. The method of claim 11, comprising changing a sweep angle based on a region of interest.

19. The method of claim 11, comprising changing an X-ray source voltage input based on object density during a sweep.

20. The method of claim 11, wherein X-ray detector is coupled to a linear stage to adjust a position based on locations of X-ray sources.

* * * * *